United States Patent [19]

Alt et al.

[11] Patent Number: 5,610,247
[45] Date of Patent: Mar. 11, 1997

[54] UNBRIDGED METALLOCENES OF 9-SUBSTITUTED FLUORENYL COMPOUNDS AND USE THEREOF

[75] Inventors: Helmut G. Alt, Bayreuth, Germany; Syriac J. Palackal, Bartlesville, Okla.; Konstantinos Patsidis, Berlin, Germany; M. Bruce Welch, Bartlesville, Okla.; Rolf L. Geerts, Bartlesville, Okla.; Eric T. Hsieh, Bartlesville, Okla.; Max P. McDaniel, Bartlesville, Okla.; Gil R. Hawley, Dewey, Okla.; Paul D. Smith, Seabrook, Tex.; Jay Janzen, Bartlesville, Okla.; Michael Schmid, Bayreuth, Germany

[73] Assignee: Phillips Petroleum Company, Bartlesville, Okla.

[21] Appl. No.: 410,154

[22] Filed: Mar. 23, 1995

Related U.S. Application Data

[63] Continuation of Ser. No. 194,944, Feb. 14, 1994, abandoned, and a continuation-in-part of Ser. No. 71,906, Jun. 3, 1993, abandoned, which is a continuation-in-part of Ser. No. 734,853, Jul. 23, 1991, Pat. No. 5,436,305.

[51] Int. Cl.$^6$ .................. C08F 4/64; C08F 10/02
[52] U.S. Cl. .............. 526/160; 526/126; 526/127; 526/170; 526/943; 556/11; 556/12; 556/52; 502/103; 502/117; 502/152
[58] Field of Search ..................... 556/43, 52, 58, 556/11, 12, 53; 526/160, 170, 352, 126, 127, 943; 502/103, 117, 152

[56] References Cited

U.S. PATENT DOCUMENTS 5,436,305 7/1995 Alt et al. ................. 526/160

FOREIGN PATENT DOCUMENTS 524624 1/1993 European Pat. Off. .

*Primary Examiner*—Fred Teskin
*Attorney, Agent, or Firm*—Edward L. Bowman

[57] ABSTRACT

9-substituted fluorenyl-containing metallocenes and their use in the polymerization of olefins is disclosed. In addition, novel 9-cyclohexylfluorenyl or 9-phenylfluorenyl compounds are disclosed. Also methods for preparing such 9-substituted fluorenyl compounds are presented.

36 Claims, No Drawings

UNBRIDGED METALLOCENES OF 9-SUBSTITUTED FLUORENYL COMPOUNDS AND USE THEREOF

This application is a continuation of U.S. application Ser. No. 08/194,944 filed Feb. 14, 1994, now abandoned, which was a continuation-in-part of U.S. application Ser. No. 08/071,906, filed Jun. 3, 1993, now abandoned as a continuation-in-part of U.S. application Ser. No. 07/734,853, filed Jul. 23, 1991, now U.S. Pat. No. 5,436,305, the disclosures of which are incorporated herein by reference.

This invention relates to fluorenyl compounds. Another aspect of this invention relates to fluorenyl compounds having substitutes at the 9 position. In still another aspect the present invention relates to the preparation of metallocenes with such fluorenyl compounds and the use of such metallocenes in the polymerization of olefins.

BACKGROUND OF THE INVENTION

Since the discovery of ferrocene in 1951, a number of metallocenes have been prepared by the combination of compounds having cyclopentadiene structure with various transition metals. The term "cyclopentadiene structure" as used herein refers to the following structure.

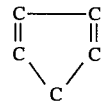

The term "cyclopentadiene-type compounds" as used herein refers to compounds containing the cyclopentadiene structure. Examples include unsubstituted cyclopentadiene, unsubstituted indene, unsubstituted fluorene, tetrahydroindene, and substituted varieties of such compounds.

Many of the cyclopentadienyl-type metallocenes have been found useful in catalyst systems for the polymerization of olefins. It has been noted in the art that variations in the chemical structure of such cyclopentadienyl-type metallocenes can have significant effects upon the suitability of the metallocenes as a polymerization catalyst. For example, the size and substitutions on cyclopentadienyl-type ligands has been found to affect the activity of the catalyst, the stereoselectivity of the catalyst, the stability of the catalyst, and other properties of the resulting polymer; however, the effects of various substituents is still largely an empirical matter, that is, experiments must be conducted in order to determine just what affect a particular variation will have upon a particular type of cyclopentadienyl-type metallocene. Some examples of some cyclopentadienyl-type metallocenes are disclosed in U.S. Pat. Nos. 4,530,914; 4,808,561; and 4,892,851, the disclosures of which are incorporated herein by reference.

Metallocenes in which two of the metal bound cyclopentadienyl type groups are connected by a bridging structure are referred to bridged metallocenes. Metallocenes in which the metal bound cyclopentadienyl type groups are not connected by bridging structure are referred to as unbridged metallocenes.

While there are references in the prior art which have envisioned metallocenes containing fluorenyl groups, only a very limited number of fluorenyl-containing metallocenes have actually been prepared prior to the present invention. The Journal of Organometallic Chemistry, Vol. 113, pages 331–339 (1976), the disclosure of which is incorporated herein by reference, discloses preparing bis-fluorenyl zirconium dichloride and bis-fluorenyl zirconium dimethyl. U.S. Pat. No. 4,892,851 and the New Journal of Chemistry, Vol. 14, pages 499–503, dated 1990, the disclosures of which are incorporated herein by reference, each disclose preparing a metallocene from the ligand 1,1-dimethylmethylene-1-(fluorenyl)-1-(cyclopentadienyl). The New Journal of Chemistry article also discloses preparing a similar compound in which the cyclopentadienyl radical has a methyl substituent in the number 3 position. The term "fluorenyl" as used herein refers to 9-fluorenyl unless indicated otherwise.

An object of the present invention is to provide new fluorenyl-containing compounds and metallocenes.

Another object is to provide a process for the polymerization of olefins using such metallocenes.

SUMMARY OF THE INVENTION

In accordance with some aspects of the present invention, there is provided, what are believed to be, new 9-substituted fluorenyl compounds. In accordance with another aspect of the present invention, there is provided a method for preparing 9-cyclohexylfluorenyl by reacting fluorenyl compounds with an alkali metal alkyl and a cyclohexyl halide. In accordance with yet another aspect of the present invention, there is provided a method for preparing 9-phenylfluorenyl compounds comprising first preparing the 9-cyclohexyl compound as described in the preceding sentence and then reducing the 9-cyclohexylfluorenyl compound with a palladium on carbon catalyst. In accordance with still another aspect of the present invention, the 9-substituted fluorenyl compounds are used to prepare unbridged metallocene by reacting an alkali metal salt of the 9-substituted fluorenyl with a suitable transition metal compound. In accordance with still another aspect of the present invention, there is provided a method for polymerizing olefins comprising contacting an olefin with the resulting metallocene under suitable conditions. In accordance with still another aspect of the present invention, there is provided the polymers produced by polymerization with such metallocenes.

DETAILED DESCRIPTION OF THE INVENTION

In accordance with the present invention, metallocenes are produced having the formula $(FlR_n)(CpR_m)MeQ_k$ wherein Fl is a 9-fluorenyl radical, Cp is cyclopentadienyl, indenyl, tetrahydroindenyl, or fluorenyl radical, each R is the same or different and is an organo radical having 1 to 20 carbon atoms, Me is metal selected from the group consisting of Group IVB, VB, and VIB metals of the Periodic Table, each Q is the same or different and is selected from the group consisting of hydrocarbyl, or hydrocarbyloxy radicals having 1 to 20 carbon atoms and halogens, k is a number sufficient to fill out the remaining valences of Me, n is a number in the range of 1 to 7, and m is a number in the range of 0 to 7; wherein at least one R on $FlR_n$ is at the 9 position of the fluorenyl radical.

Metallocenes of this type can be prepared by reacting an alkali metal salt of the 9-substituted fluorenyl compound with a suitable transition metal compound in a suitable solvent under suitable reaction conditions. In some cases, it has been noted that if the substituent at the 9 position is too bulky, the desired metallocene is not obtained when the fluorenyl salt is reacted with cyclopentadienyl zirconium trichloride. Examples of such substituents include 9-diphenylmethyl, 9-diphenylmethylsilyl, and 9-mesityl. However, the process is suitable for making (9-trimethylsilyl-2,7-di-t-tert butyl fluorenyl) (cyclopentadienyl) zirconium dichloride and (9-o-tolylfluorenyl) (cyclopentadienyl) zirconium dichloride.

The term "transition metal compound" as used herein includes compounds of the formula $MeQ_k$ wherein Me, Q, and k are as defined above. Some non-limiting examples include titanium tetrachloride, zirconium tetrachloride, hafnium tetrachloride, cyclopentadienyl zirconium trichloride, fluorenyl zirconium trichloride, indenyl zirconium trichloride, 3-methylcyclopentadienyl zirconium trichloride, 4-methylfluorenyl zirconium trichloride, and the like.

Metallocenes in which Q is other than a halogen can be readily prepared by reacting the halide form of a metallocene with an alkali metal salt of a hydrocarbyloxy radical under conditions as have been used in the past performing such ligands in prior art metallocenes. See, for example, the aforementioned J. Organomet. Chem., 113, 331–339 (1976). This technique has been used to produce (9-substituted fluorenyl) (cyclopentadienyl) zirconium dimethyl when the 9 substituent on the fluorenyl is methyl, isopropyl, phenyl, or trimethyl silyl. Another approach involves reacting a compound of the formula $MQ_k$ wherein at least one Q is hydrocarbyl or hydrocarbyloxy with the alkali metal salt of the fluorenyl compound.

In accordance with the preferred embodiment of the present invention, the reaction between the fluorenyl-containing salt and the transition metal compound is carried out in the presence of a liquid diluent is non-halogenated and non-coordinating toward the transition metal compound. Examples of such suitable liquids include hydrocarbons such as toluene, pentane, or hexane, as well as non-cyclic ether compounds such as diethylether. It has been found the use of such non-halogenated non-coordinating solvents generally allows one to obtain large amounts of substantially pure metallocenes and in a more stable form, and also often allows the reaction to be conducted under higher temperatures than when THF is used as the diluent. In an especially preferred embodiment, the fluorenyl-containing salt used as the ligand for preparing the metallocene is also prepared in a liquid diluent that is non-halogenated and non-coordinating toward the transition metal.

The alkali metal salt of the 9-substituted fluorenyl compound can be formed using generally any technique known in the art. For example, such can be prepared by reacting an alkali metal alkyl with the 9-substituted fluorenyl compound. The molar ratio of the alkali metal alkyl to the fluorenyl compound can vary, generally however, the ratio would be in the range of about 0.5/1 to about 1.5/1, still more preferably about 1/1. Typically the alkali metal of the alkali metal alkyl would be selected from sodium, potassium, and lithium, and the alkyl group would have 1 to 8 carbon atoms, more preferably 1 to 4 carbon atoms. Preferably if the fluorenyl salt is formed using tetrahydrofuran (THF) as the liquid diluent, the salt is isolated and substantially all the THF is removed before the salt is contacted with the transition metal halide. The molar ratio of the 9-substituted fluorenyl compound to the transition metal compound can vary over a wide range depending upon the particular results desired. Typically however, the molar ratio of the 9-substituted fluorenyl compound to the transition metal would be in the range of from about 1/1 to about 2/1.

The resulting metallocene can be recovered and purified using conventional techniques known in the art such as filtration, extraction, crystallization, and recrystallization. It is generally desirable to recover the metallocene in a form that is free of any substantial amount of by-product impurities. Accordingly, recrystallization and fractional crystallization to obtain relatively pure metallocenes may be desirable. Dichloromethane has been found to be particularly useful for such recrystallizations. It is generally desirable to use the metallocenes soon after their preparation or at least to store the metallocenes under conditions favoring their stability. For example, metallocenes can generally be stored in the dark at low temperature, i.e. below 0° C. in the absence of oxygen or water.

Some 9-substituted fluorenyl compounds are known. Examples include 9-t-butyl fluorene (Can. J. Chem., 34 991–1005 (1956)), and 9-phenyl fluorene (Chem. Berichte 5, 908 (1872)). A number 9-alkyl fluorene compounds can be prepared by reacting fluorene with butyllithium to form the fluorenyl lithium and then adding the corresponding alkyl halide. In some cases, higher yields can be obtained by using tetrahydrofuran as the solvent rather than non-polar solvents such as hexane. Such a process has been used to prepare the 9-substituted fluorene using the following halides: methyl chloride, ethyl chloride, isopropyl chloride, benzyl chloride, diphenylmethyl chloride, trimethyl silyl chloride, and diphenyl methyl silyl chloride. The same procedure also works on many substituted fluorene compounds. For example, 9-trimethyl silyl fluorene compounds have been prepared such as the 2,7-dimethyl, the 2,7-diethyl, and the 2,7-dibromo. This direct alkylation process is not particularly useful for preparing 9-tertiary alkyl or 9-aryl substituted fluorenes. In order to produce those compounds one can react fluorenone with the necessary Grignard reagent and then the resulting 9-substituted hydroxyfluorene can be reduced to yield the 9-substituted fluorene. Such techniques have been disclosed in Chem. Ges, 64 917 (1931) and J. Chem. Soc. B. 173 (1970). Instead of using iodine or zinc/HCl as the reducing agent, preferably a $BF_3 \cdot Et_2O/Et_3SiH$ mixture such as disclosed in J. Org. Chem., 53, 2450 (1988) or Tetrahedron Lett., 11, 1345 (1968) is used. This technique of reduction permits a gentle execution of the reaction and leads to quantitative yields.

Using the described procedure starting with fluorene it was possible to produce 9-phenyl fluorene, 9-o-tolyl fluorene, 9-p-tolyl fluorene, 9-mesityl fluorene, 9-p-fluorophenyl fluorene, 9-p-methoxyphenyl fluorene, and 9-t-butylfluorene.

In accordance with another aspect of the present invention, there is provided a method for preparing 9-cyclohexylfluorenyl compounds. In accordance with this method, a fluorene compound, either substituted or unsubstituted, is reacted with an alkali metal alkyl of the type previously described to produce an alkali metal salt of the fluorenyl compound which is in turn reacted with a cyclohexylhalide to yield the desired 9-cyclohexylfluorenyl compound. Examples of such fluorene compounds that can be reacted to yield the 9-cyclohexylfluorenyl compound include, for example, unsubstituted fluorene, 4-methylfluorene, 2,7-dimethylfluorene, 2,7-ditertiarybutylfluorene, 3-tertiarybutylfluorene, 2-methylfluorene, and the like.

In accordance with still another aspect of the present invention, the resulting 9-cyclohexylfluorenyl compound can be converted into the corresponding 9-phenylfluorenyl compound by carrying out a reduction over a palladium on carbon catalyst under suitable reaction conditions.

The resulting fluorenyl containing metallocenes can be used in combination with a suitable co-catalyst for the polymerization of olefinic monomers. In such processes the metallocene or the co-catalyst can be employed on a solid insoluble particulate support.

Examples of suitable co-catalysts include generally any of those organometallic co-catalysts which have in the past been employed in conjunction with transition metal containing olefin polymerization catalysts. Some typical examples include organometallic compounds of metals of Groups IA, IIA, and IIIB of the Periodic Table. Examples of such compounds have included organometallic halide compounds, organometallic hydrides and even metal hydrides. Some specific examples include triethylaluminum, triisobutylaluminum, diethylaluminum chloride, diethylaluminum hydride, and the like. The most commonly used cocatalyst for metallocenes is aluminoxane.

Recently, aluminum-free catalyst systems based on metallocenes have been developed. One example is the combination of metallocene dimethyl complexes with Lewis acids such as disclosed in *Organometallics*, 10, 840 (1991); *J. Am. Chem. Soc.*, 113, 3625 (1991); *Organometallics*, 10, 3910 (1991); *J. Organometallic Chem.*, 424, C5 (1992) and 423, C1 (1992); and *J. Am. Chem. Soc.*, 113, 8570 (1991). Cationic complexes of the [Cp$_2$MMe][A] type (M=Ti, Zr, HF; A=e.g. BP$_4$, [B(C$_6$F$_5$)$_4$]$^-$; and Me=methyl) have also been found to be an alternative to the metallocene dichloride/MAO catalyst systems. Some examples of such catalyst systems are disclosed in *J. Am. Chem. Soc.*, 109, 4111 (1987); *J. Catal.*, 3, 80 (1964), 3, 89 (1964); and 3, 99 (1964); and *Organometallics*, 11, 362 (1992).

The currently most preferred co-catalyst is an aluminoxane. Such compounds include those compounds having repeating units of the formula

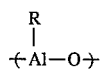

where R is an alkyl group generally having 1 to 5 carbon atoms. Aluminoxanes, also sometimes referred to as poly-(hydrocarbyl aluminum oxides) are well known in the art and are generally prepared by reacting an organo hydrocarbylaluminum compound with water. Such a preparation techniques are disclosed in U.S. Pat. Nos. 3,242,099 and 4,808,561, the disclosures of which are incorporated herein by reference. The currently preferred co-catalysts are prepared either from trimethylaluminum or triethylaluminum, sometimes referred to as poly(methylaluminum oxide) and poly(ethylaluminum oxide), respectively. It is also within the scope of the invention to use an aluminoxane in combination with a trialkylaluminum, such as disclosed in U.S. Pat. No. 4,794,096, the disclosure of which is incorporated herein by reference.

The fluorenyl-containing metallocenes in combination with the aluminoxane co-catalyst can be used to polymerize olefins. Generally such polymerizations would be carried out in a homogeneous system in which the catalyst and co-catalyst were soluble; however, it is within the scope of the present invention to carry out the polymerizations in the presence of supported forms of the catalyst and/or co-catalyst in a slurry or gas phase polymerization. It is within the scope of the invention to use a mixture of two or more fluorenyl-containing metallocenes or a mixture of an inventive fluorenyl-containing metallocene with one or more other cyclopentadienyl-type metallocenes.

The fluorenyl-containing metallocenes when used with aluminoxane are particularly useful for the polymerization of mono-unsaturated aliphatic alpha-olefins having 2 to 10 carbon atoms. Examples of such olefins include ethylene, propylene, butene-1, pentene-1, 3-methylbutene-1, hexene-1, 4-methylpentene-1, 3-ethylbutene-1, heptene-1, octene-1, decene-1, 4,4-dimethyl-1-pentene, 4,4-diethyl-1-hexene, 3-4-dimethyl-1-hexene, and the like and mixtures thereof. Using the catalysts for preparing copolymers of ethylene and propylene or polymers of ethylene and/or propylene and generally a minor amount, i.e. no more than about 12 mole percent, more typically less than about 10 mole percent, of a higher molecular weight olefin is also contemplated.

The polymerizations can be carried out under a wide range of conditions depending upon the particular metallocene employed, and the results desired. Examples of typical conditions under which the metallocenes can be used in the polymerization of olefins include conditions such as disclosed in U.S. Pat. Nos. 3,242,099; 4,892,851; and 4,530,914; the disclosures of which are incorporated herein by reference. It is considered that generally any of the polymerization procedures used in the prior art with any transition metal based catalyst systems can be employed with the present fluorenyl-containing metallocenes.

Generally the molar ratio of the aluminum in the aluminoxane to the transition metal in the metallocene particularly in slurry or solution polymerization would be in the range of about 0.1:1 to about 10$^5$:1 and more preferably about 5:1 to about 10$^4$:1. As a general rule, the polymerizations would be carried out in the presence of liquid diluents which do not have an adverse affect upon the catalyst system. Examples of such liquid diluents include butane, isobutane, pentane, hexane, heptane, octane, cyclohexane, methylcyclohexane, toluene, xylene, and the like. The polymerization temperature can vary over a wide range, temperature typically would be in the range of about −60° C. to about 280° C., more preferably in the range of about 20° C. to about 160° C. Typically the pressure would be in the range of from about 1 to about 500 atmospheres or greater. It is often particularly desirable to carry out the polymerization in the presence of hydrogen. The amount of hydrogen needed for best results can be readily determined by routine experimentation.

The polymers produced with this invention have a wide range of uses that will be apparent to those skilled in the art from the physical properties of the respective polymer.

A further understanding of the present invention, its various aspects, objects, and advantages will be provided by the following examples.

EXAMPLE I 20 grams of unsubstituted fluorene was combined with 200 mL of THF to form a solution. Then 75 mL of a 1.6M hexane solution of N-butyllithium was slowly added dropwise to the solution at room temperature. After the dropwise addition, the mixture was stirred for a further period of one hour at room temperature and then the reaction mixture was cooled to −78° C. Then 29.5 grams of bromocyclohexane was added and the system was allowed to warm up to room temperature. The mixture was stirred for two more hours at room temperature and then washed with saturated aqueous ammonium chloride solution and then twice with distilled water. After drying the organic phase over Na$_2$SO$_4$, the solvent was removed in a vacuum generated by a jet of flowing water. The residue was then dissolved in 70 mL of pentane and recrystallized at −30° C. A product in the form of colorless needles was obtained. The product was subjected to H$^1$NMR, C$^{13}$NMR and mass spectroscopy for identification. The results were consistent with the compound 9-cyclohexylfluorene.

EXAMPLE II 20 grams of the 9-cyclohexylfluorene was mixed with 1 gram of a palladium/carbon catalyst containing 10 wt.

percent palladium and dehydrogenated for 12 hours at 300° C. The residue from the reaction was eluted with THF and suspension filtered in order to separate the catalyst. After concentrating the solution by evaporation, the yellow to orange residue was purified over silica gel. Pentane was used as the solvent. The product was subjected to analysis as in Example I and was found to have a structure consistent with 9-phenylfluorene.

EXAMPLE III 4-methyl-9-cyclohexylfluorene was prepared from 4-methylfluorene using a method analogous to that used in Example I. Some of the resulting 4-methyl-9-cyclohexylfluorene was then subjected to a reduction analogous to that used in Example II. The dehydrogenation differed in that in this case it was carried out for 24 hours. The product was recrystallized in 150 mL of pentane to obtain a colorless powder which had a structure consistent with 4-methyl-9-phenylfluorene.

EXAMPLE IV

Metallocenes were prepared by reacting the 9-substituted fluorenyl compounds produced in Examples I–III by reacting the specific 9-substituted fluorene compound with one mole equivalent of butyllithium using a 1.6M hexane solution of the butyllithium. The mixture was then stirred at room temperature until the evolution of gas had ended. Half of one mole equivalent of zirconium tetrachloride was then added and the mixture was stirred for 30 to 60 minutes. The solution was decanted and the residue washed with diethylether and then dried. This process produced the following metallocenes, namely bis-9-cyclohexylfluorenyl zirconium dichloride, bis-9-phenylfluorenyl zirconium dichloride, bis-9-cyclohexyl-4-methylfluorenyl zirconium dichloride, and bis-9-phenyl-4-methylfluorenyl zirconium dichloride.

In order to convert the metallocenes to dimethyl metallocenes, the metallocene dichloride complex in each case was suspended in toluene and mixed with two mole equivalents of methyllithium. The resulting mixture was stirred at room temperature until the color changed. Filtration over sodium sulfate was then used and after removing the solvent, the solid was recrystallized in hexane.

EXAMPLE V

Using a procedure similar to that used in Example I, other 9-substituted fluorenyl compounds were prepared. Specifically 9-trimethylsilylfluorenyl, 9-isopropylfluorenyl, 9-trimethylsilyl-2,7-ditertiarybutylfluorenyl.

EXAMPLE VI

A series of metallocenes were prepared for evaluation in the polymerization of ethylene, namely:

| Catalyst |
|---|
| A (9-phenylfluorenyl)(cyclopentadienyl)$ZrCl_2$ |
| B (9-cyclohexylfluorenyl)(cyclopentadienyl)$ZrCl_2$ |
| C (9-isopropylfluorenyl)(cyclopentadienyl)$ZrCl_2$ |
| D (9-trimethylsilylfluorenyl)(cyclopentadienyl)$ZrCl_2$ |
| E bis(4-methyl-9-phenyl fluorenyl)$ZrCl_2$ |
| F bis(9-phenylfluorenyl)$ZrCl_2$ |
| G bis(9-cyclohexylfluorenyl)$ZrCl_2$ |
| H (fluorenyl)(cyclopentadienyl)$ZrCl_2$ |
| I bis(fluorenyl)$ZrCl_2$ |

The (9-substituted fluorenyl) (cyclopentadienyl) metallocenes were made by reacting an alkali metal salt of the respective 9-substituted fluorenyl compound with cyclopentadienyl zirconium trichloride.

The ethylene polymerizations were conducted for one hour at 90° C. in a 3.8 liter stirred, stainless steel reactor in the presence of isobutane diluent, hydrogen as a molecular weight control agent, and soluble methyl aluminoxane as the cocatalyst. First the metallocene catalyst was weighed in a dry box and dissolved in a toluene solution of methyl aluminoxane. The toluene methyl aluminoxane solution was prepared by diluting a 1.7M toluene solution of methyl aluminoxane, purchased from Ethyl Corporation, to the desired concentration. Amounts were selected so that the final Al/Zr molar ratio was in the range of 400–1400/1. The charge order was metallocene/methyl aluminoxane solution and then 2 liters of isobutane. After heating these materials to 90° C., hydrogen was added in the amount of a 10 psi pressure drop from a 300 cc cylinder, and then ethylene was introduced so that the total reactor pressure was maintained at 450 psig for the entire hour. Ethylene was supplied on demand from a pressured reservoir as required during each run. Polymerization was terminated by venting ethylene and diluent. The polymer was recovered, dried and weighed to determine yields. Catalyst productivity was calculated by dividing polymer weight in grams by the weight of metallocene used in grams, and by the weight of zirconium used in grams, and by the weight of metallocene plus methyl aluminoxane in grams and is conveniently expressed as kg polymer per g desired catalyst component per hour (kg/g/hr.). The results are summarized in the following table:

TABLE I

| Catalyst No. | mg | MAO/Zr molar | Productivity | | | MI g/10 min | HLMI/MI (HLMI) |
| | | | g/g met./1000 | g/g Zr/1000 | g/gmet + MAC | | |
|---|---|---|---|---|---|---|---|
| A | 0.223 | 787 | 323 | 1662 | 3300 | 1.44 | 48.3 |
| B | 0.209 | 1434 | 621 | 3230 | 3520 | too low | (0.006) |
| C | 0.196 | 1018 | 559 | 2737 | 4200 | too low | (0.97) |
| D | 0.2 | 816 | 177 | 902 | 1720 | 1.1 | 57.8 |
| E | 0.89 | 482 | 0.6 | 4 | 13 | — | — |
| F | 0.74 | 552 | 2.5 | 18 | 50 | — | — |
| G | 0.9 | 465 | 4.6 | 32 | 108 | — | — |
| H | 0.272 | 921 | 235 | 1012 | 1716 | 1.5 | 65.4 |
| H | 0.296 | 845 | 293 | 1262 | 2330 | 0.11 | 91.9 |
| I | 1.35 | 464 | 16 | 9 | 295 | 1.74 | 114 |

The results demonstrate that the (9-substituted fluorenyl) (cyclopentadienyl) zirconium dichloride metallocenes A, B, and C were much more active than the unsubstituted (fluorenyl) (cyclopentadienyl) zirconium dichloride catalyst, i.e. H. The (9-trimethylsilylfluorenyl) metallocene of Catalyst D was also very active but only for the first few minutes of the polymerization.

Polyethylene obtained using (9-cyclohexylfluorenyl) (cyclopentadienyl zirconium dichloride, i.e. Catalyst B at lower temperature and pressure in the absence of $H_2$ was particularly interesting in that it did not appear to melt in a melt indexer at 190° C. and it had a unusually narrow molecular weight distribution particularly for a polymer having such a high molecular weight. The initial DSC scan indicated a $T_m$ of 141.5° C. Size exclusion chromatography indicated a $M_w/M_n$ of 2.61. Its weight average molecular weight ($M_w$) was 1,850,000.

The bis(9-substituted fluorenyl) metallocenes E–G did not appear to have any major advantage over the bis(unsubstituted) fluorenyl metallocene I in activity; however, they did produce a polyethylene polymer.

EXAMPLE VII

Using MAO as a cocatalyst under generally similar conditions to those used in Example VI it has been determined that both (9-methyl fluorenyl) (cyclopentadienyl) zirconium dichloride and (9-t-butyl fluorenyl) (cyclopentadienyl) zirconium dichloride are useful for the polymerization of ethylene. Both have also been similarly used for the copolymerization of ethylene and 1-hexane. In both homopolymerization and copolymerization it is considered desirable to use hydrogen in the polymerization.

EXAMPLE VIII

A number of the inventive 9-substituted fluorenyl metallocenes were also evaluated as catalysts for the polymerization of propylene. The metallocene dichloride was dissolved in toluene and mixed with a commercial methylaluminoxane (MAO) solution. The formation of the polymerization-active metallocene methyl cation catalyst system expresses itself by a color change. For the purpose of drying, 500 ml of liquid propylene in an autoclave was mixed with 10 ml of the MAO solution and stirred for 30 minutes at 20° C. Then the autoclave was cooled down to −10° C. and the catalyst solution was added. Then the autoclave was heated up to 60° C. and held at that temperature for 1 hour and then the polymerization was stopped. The metallocenes (9-isopropylfluorenyl) (cyclopentadienyl) zirconium dichloride and (9-cyclohexylfluorenyl) (cyclopentadienyl) zirconium dichloride resulted in polypropylene that appeared to be atactic.

That which is claimed is:

1. An unbridged metallocene of the formula ($FlR_n$) ($CpR_m$) $MeQ_2$ wherein Fl is a 9-fluorenyl radical, Cp is selected from the group consisting of cyclopentadienyl, indenyl, tetrahydroindenyl, and fluorenyl radicals, each R is either the same or different organo radical having 1 to 20 carbon atoms, Me is a metal selected from the Group IVB metals, each Q is the same or different and is selected from the group consisting of hydrocarbyl or hydrocarbyloxy radicals having 1 to 20 carbon atoms and halogen, n is a number in the range of 1 to 7, and m is a number in the range of 0 to 7; wherein at least one R on $FlR_n$ is at the 9 position of the 9-fluorenyl radical.

2. A metallocene according to claim 1 wherein there is a 9-cyclohexyl group at the 9 position of the 9-fluorenyl radical.

3. A metallocene according to claim 2 wherein Me is Zr and Q is Cl.

4. A metallocene according to claim 3 named bis(9-cyclohexylfluorenyl) zirconium dichloride.

5. A metallocene according to claim 3 named (9-cyclohexylfluorenyl) (cyclopentadienyl) zirconium dichloride.

6. A metallocene according to claim 3 named bis(9-cyclohexyl-4-methylfluorenyl) zirconium dichloride.

7. A metallocene according to claim 1 wherein $FlR_n$ has a 9-phenyl group.

8. A metallocene according to claim 7 named bis(9-phenylfluorenyl) zirconium dichloride.

9. A metallocene according to claim 7 named (9-phenylfluorenyl) (cyclopentadienyl) zirconium dichloride.

10. A metallocene according to claim 7 named bis(9-phenyl-4-methylfluorenyl) zirconium dichloride.

11. A metallocene according to claim 1 named (9-isopropylfluorenyl) (cyclopentadienyl) zirconium dichloride.

12. A metallocene according to claim 1 named (9-trimethylsilylfluorenyl) (cyclopentadienyl) zirconium dichloride.

13. A metallocene according to claim 1 wherein CpRm is cyclopentadienyl, Me is Zr, and Q is Cl.

14. A metallocene according to claim 13 wherein FlRn is a 9-substituted fluorenyl having no other substituents.

15. A metallocene according to claim 14 wherein the substituent on the 9 position of FlRn is selected from the group consisting of methyl, isopropyl, t-butyl, cyclohexyl, phenyl, o-tolyl, p-tolyl, p-fluorophenyl, and trimethylsilyl.

16. A metallocene according to claim 1 named (9-trimethylsilyl-2,7-di-tert-butyl fluorenyl) cyclopentadienyl) zirconium dichloride.

17. A metallocene according to claim 1 wherein FlRn and CpRm are the same and Q is Cl.

18. A metallocene according to claim 17 wherein FlRn is selected from the group consisting of 9-methyl fluorenyl, 9-isopropyl fluorenyl, and 9-trimethyl fluorenyl.

19. A metallocene according to claim 1 wherein Cp is indenyl.

20. A metallocene according to claim 19 wherein m is 0.

21. A metallocene according to claim 20 wherein ($FlR_n$) is selected from the group consisting of 9-methyl fluorenyl, 9-isopropyl fluorenyl, and 9-trimethylsilyl fluorenyl.

22. A process for preparing a polymer comprising contacting an olefin under suitable reaction conditions with a metallocene of claim 1.

23. A process according to claim 22 wherein the polymerization is conducted using (9-cyclohexylfluorenyl) (cyclopentadienyl) zirconium dichloride.

24. A process according to claim 22 wherein the polymerization is conducted using (9-phenylfluorenyl) (cyclopentadienyl) zirconium dichloride.

25. A process according to claim 22 wherein the polymerization is conducted using (9-isopropylfluorenyl) (cyclopentadienyl) zirconium dichloride.

26. A process according to claim 22 wherein the polymerization is conducted using (9-trimethylsilylfluorenyl) (cyclopentadienyl) zirconium dichloride.

27. A process according to claim 22 wherein the polymerization is conducted using (9-trimethylsilyl-2,7-di-tert-butyl fluorenyl) (cyclopentadienyl) zirconium dichloride.

28. A process according to claim 22 wherein ($CpR_m$) is pentamethylcyclopentadienyl.

29. A process according to claim 22 wherein the polymerization is conducted using (9-tert-butyl fluorenyl) (cyclopentadienyl) zirconium dichloride.

30. A process according to claim 22 wherein the polymerization is conducted using (9-methyl fluorenyl) (cyclopentadienyl) zirconium dichloride.

31. A process according to claim 22 wherein the polymerization is conducted using bis(9-cyclohexylfluorenyl) zirconium dichloride.

32. A process according to claim 22 wherein the polymerization is conducted using bis(9-phenylfluorenyl) zirconium dichloride.

33. A process according to claim 22 wherein ethylene is polymerized.

34. A process according to claim 22 wherein the polymerization is conducted using a metallocene in which Cp is indenyl.

35. A process according to claim 34 wherein m is 0.

36. A process according to claim 35 wherein $(FR_n)$ is selected from the group consisting of 9-methyl fluorenyl, 9-isopropyl fluorenyl, and 9-trimethylsilyl fluorenyl.

* * * * *

UNITED STATES PATENT AND TRADEMARK OFFICE
CERTIFICATE OF CORRECTION

PATENT NO. : 5,610,247
DATED : March 11, 1997
INVENTOR(S) : Helmut G. Alt et al

It is certified that error appears in the above-indentified patent and that said Letters Patent is hereby corrected as shown below:

Column 10, claim 18, line 3, after "9-trimethyl" please insert ---silyl---.

Signed and Sealed this

Nineteenth Day of August, 1997

*Attest:*

BRUCE LEHMAN

*Attesting Officer*  Commissioner of Patents and Trademarks